United States Patent
Ha et al.

(10) Patent No.: US 10,232,000 B2
(45) Date of Patent: Mar. 19, 2019

(54) STEM CELLS DERIVED FROM BASAL PORTION OF CHORIONIC TROPHOBLAST LAYER AND CELL THERAPY COMPRISING SAME

(71) Applicant: Samsung Life Public Welfare Foundation, Seoul (KR)

(72) Inventors: Chul Won Ha, Seoul (KR); Jin A. Kim, Gyeonggi-do (KR)

(73) Assignee: Samsung Life Public Welfare Foundation, Seoul (KR)

( * ) Notice: Subject to any disclaimer, the term of this patent is extended or adjusted under 35 U.S.C. 154(b) by 144 days.

(21) Appl. No.: 15/110,668

(22) PCT Filed: Jan. 8, 2015

(86) PCT No.: PCT/KR2015/000205
§ 371 (c)(1),
(2) Date: Jul. 8, 2016

(87) PCT Pub. No.: WO2015/105357
PCT Pub. Date: Jul. 16, 2015

(65) Prior Publication Data
US 2016/0324901 A1 Nov. 10, 2016

(30) Foreign Application Priority Data
Jan. 8, 2014 (KR) .................. 10-2014-0002316

(51) Int. Cl.
| A61K 35/50 | (2015.01) |
| C12N 5/071 | (2010.01) |
| C12N 5/073 | (2010.01) |
| A61K 35/28 | (2015.01) |
| A61K 35/51 | (2015.01) |
| C12N 5/074 | (2010.01) |
| A61K 35/12 | (2015.01) |

(52) U.S. Cl.
CPC .............. *A61K 35/50* (2013.01); *A61K 35/28* (2013.01); *A61K 35/51* (2013.01); *C12N 5/0605* (2013.01); *C12N 5/0607* (2013.01); *A61K 2035/124* (2013.01); *C12N 2506/025* (2013.01)

(58) Field of Classification Search
CPC .............................. A61K 35/50; C12N 5/0605
See application file for complete search history.

(56) References Cited

U.S. PATENT DOCUMENTS

| 8,057,788 B2 * | 11/2011 | Hariri | .................. C12N 5/0605 424/93.1 |
| 2006/0211110 A1 | 9/2006 | Lee et al. | |
| 2007/0243172 A1 | 10/2007 | Ra et al. | |
| 2016/0326487 A1 | 11/2016 | Ha et al. | |

FOREIGN PATENT DOCUMENTS

| KR | 10-0818214 | 4/2008 |
| WO | WO 2008/051568 | 2/2008 |
| WO | WO 2008/146991 | 4/2008 |
| WO | WO 2012/008733 | 1/2012 |

OTHER PUBLICATIONS

Parolini et al., Concise review: Isolation and characterization of cells from human term placenta: Outcome of the first international workshop on placenta derived stem cells. Stem Cell, vol. 26, No. 2 (Feb. 2008) pp. 300-311.*
International Search Report corresponding to International Patent Application No. PCT/KR15/00204, dated Mar. 24, 2015.
International Search Report corresponding to International Patent Application No. PCT/KR15/00205, dated Mar. 25, 2015.
C. Pipino et al., "Placenta as a reservoir of stem cells: an underutilized resource?," Nov. 25, 2012, British Medical Bulletin, vol. 105, pp. 43-67.

* cited by examiner

*Primary Examiner* — Kara D Johnson
(74) *Attorney, Agent, or Firm* — Leydig, Voit & Mayer, Ltd.

(57) ABSTRACT

The present disclosure relates to stem cells derived from the basal portion of the chorionic trophoblast layer (bCT), which is a part of the issues of the placenta, and cell therapy comprising same. Stem cells derived from the basal portion of the chorionic trophoblast layer according to the present invention exhibit uniform growth characteristic, and superb proliferation and differentiation characteristic as compared with the conventional stem cells derived from the full placenta or other tissues, and exhibit excellent tissue regeneration effect in an animal model, thus can be effectively used in cell therapy.

10 Claims, 14 Drawing Sheets

STEM CELLS DERIVED FROM BASAL PORTION OF CHORIONIC TROPHOBLAST LAYER AND CELL THERAPY COMPRISING SAME

CROSS-REFERENCE TO RELATED APPLICATIONS

This application is a U.S. National Stage Application under 35 U.S.C. § 371 of International Application No. PCT/KR2015/000205, filed Jan. 8, 2015, which claims the benefit of and priority to Korean Patent Application No. 10-2014-0002316, filed Jan. 8, 2014. Each of these applications is hereby incorporated by reference in its entirety.

TECHNICAL FIELD

The present disclosure provides stem cells derived from a basal portion of chorionic trophoblast layer (bCT) which is a part of the tissues of the placenta, and a cell therapy including the same.

BACKGROUND ART

Recently, biotechnology has proposed the possibility of new solutions to the food, environmental, and health problems as a final goal of human welfare, and among them, a technique using stem cells is emerging as a new technique of incurable disease treatment. For this disease treatment of the human, organ transplantation, gene therapy, and the like have been proposed before, but efficient commercialization is not sufficient due to immune rejection, supplied organs shortage, and lack of knowledge about vector development or disease genes. As a result, an interest in the stem cells is increased, and totipotent stem cells having ability to generate all organs through proliferation and differentiation are recognized to treat most of diseases and essentially solve organ damage. Further, many scientists have variously proposed potential to the stem cells up to treatments of Parkinson's disease which has been incurable, various cancers, diabetes and spinal cord injuries, and the like, as well as regeneration of almost all organs of the human body.

The "stem cells" refer to cells having self-replication capacity as non-differentiated cells and a differentiation capacity into two or more different kinds of cells. The stem cells classified into embryonic stem cells and adult stem cells according to a cytological origin. The embryonic stem cells are derived from an embryo or a fetus genital tissue during generation, while the adult stem cells are derived from Bone marrow, umbilical cord blood, fat, placenta, muscle, synovium, brain, liver, pancreas, and the like which are object tissues after the fetal growth is completed. Since the embryonic stem cells have ethical issue, there is a limitation to be used as a cellular therapeutic agent, however the adult stem cells can be mainly extracted from fat, umbilical cord blood, bone marrow, placenta, and the like and have no ethical problem.

Among them, in the case of the stem cells derived from the placenta, by using the placenta discarded after parturition, it is advantageous that extraction is easy and a large amount of stem cells can be easily ensured. The stem cells derived from the fat or the bone marrow are influenced by ages or health states of donors to be isolated and extracted to have a limitation in proliferation or differentiation capacity and have large variability. However, the ability of the stem cells derived from the placenta are not almost influenced according to parameters such as ages of donors as stem cells which may be obtained in the earliest stage among the adult stem cells, and also, such stem cells have excellent proliferation and differentiation abilities. Further, from the stem cells derived from the placenta, a stem cell group which can be used for various diseases such as nervous system disorders, liver diseases, and musculo skeletal diseases may be isolated.

Due to the aforementioned advantages, researches on the stem cells derived from the placenta have been actively conducted. For example, in Korea Patent Registration No. 818214, a method of isolating stem cells from an amniotic membrane or a decidua by using a medium including N-acetyl-L-cysteine (NAC) is proposed, and in Korea Patent Registration No. 871984, a method of culturing stem cells derived from an amniotic membrane, a serous membrane, a basal decidua, and a placenta tissue by using a medium including a basic fibroblast growth factor (bFGF) is proposed. However, until now, researches on stem cells derived from a basal portion of chorionic trophoblast layer which is a part of the tissues of the placenta are not yet conducted.

DISCLOSURE

Technical Problem

Under such circumstances, the present inventors have made intensive studies to develop stem cells having more excellent stem cell capacity from the stem cells derived from the placenta. As a result, present inventors have completed the present disclosure by isolating a basal portion of chorionic trophoblast layer (bCT) which is a tissue layer corresponding to a thickness of about 25% as a portion adjacent to a chorionic membrane in a total chorionic trophoblast layer (tCT) of the placenta to prepare stem cells derived from the basal portion of chorionic trophoblast layer and verifying that the stem cells derived from the basal portion of chorionic trophoblast layer (bCT) which is a part of the tissues of the placenta exhibit uniform growth characteristic, and superb proliferation and differentiation characteristics as pluripotent stem cells, as compared with the conventional stem cells derived from the whole placenta or other tissues, and exhibit an excellent tissue regeneration effect in a tissue defect animal model.

Accordingly, it is an object of this invention to provide stem cells derived from a basal portion of a chorionic trophoblast layer (bCT) which is a part of the tissues of the placenta.

It is another object of this invention to provide a cellular therapeutic agent and a composition for regenerating tissues including stem cells derived from a basal portion of chorionic trophoblast layer or cells differentiated from the stem cells as an active ingredient.

Technical Solution

An aspect of the present disclosure provides stem cells derived from a basal portion of chorionic trophoblast layer (bCT) which is a part of the tissues of the placenta.

Another aspect of the present disclosure provides a cellular therapeutic agent including stem cells derived from the basal portion of chorionic trophoblast layer (bCT) or cells differentiated from the stem cells as an active ingredient.

Yet another aspect of the present disclosure provides a composition for regenerating tissues including stem cells derived from the basal portion of chorionic trophoblast layer (bCT) or cells differentiated from the stem cells as an active ingredient.

Advantageous Effects

According to the present invention, the stem cells derived from the basal portion of the chorionic trophoblast layer can exhibit uniform growth characteristic, and superb proliferation and differentiation characteristic as compared with the conventional stem cells derived from the whole placenta or other tissues, and can exhibit an excellent tissue regeneration effect in a tissue defect animal model, and thus can be usefully used as a cellular therapeutic agent.

MODES OF THE DISCLOSURE

Hereinafter, the present disclosure will be described in detail.

The present disclosure provides stem cells derived from a basal portion of a chorionic trophoblast layer (bCT) which is a part of the tissues of the placenta.

In the present invention, the "stem cells" refer to cells having self-replication capacity and a differentiation capacity into two or more different kinds of cells. The stem cells may be classified into totipotent stem cells, pluripotent stem cells, and multipotent stem cells according to differentiation capacity.

In the present invention, the "totipotent stem cells" are cells having a totipotent property which can be differentiated to one complete object, the cells up to 8 cell stages after fertilization of the egg and the sperm have the totipotent property, and the totipotent stem cell means the cell to be differentiated into one complete object when the cells are isolated, and then, transplanted into the uterus. In the present invention, the "pluripotent stem cells" are cells which can be differentiated into various cells and tissues derived from ectoderm, mesoderm, and endoderm layers, and are derived from an inner cell mass positioned in the blastocyst shown after 4 to 5 days of the fertilization, which are called embryonic stem cells. The pluripotent stem cells mean cells which are differentiated into various different tissue cells, but do not form a new organism. In the present invention, the "multipotent stem cells" refer to cells which may be differentiated into only specific cells forming a tissue and an organ including stem cells. For the purpose of the present disclosure, the "stem cells" may be preferably the multipotent stem cells.

Figure 1:
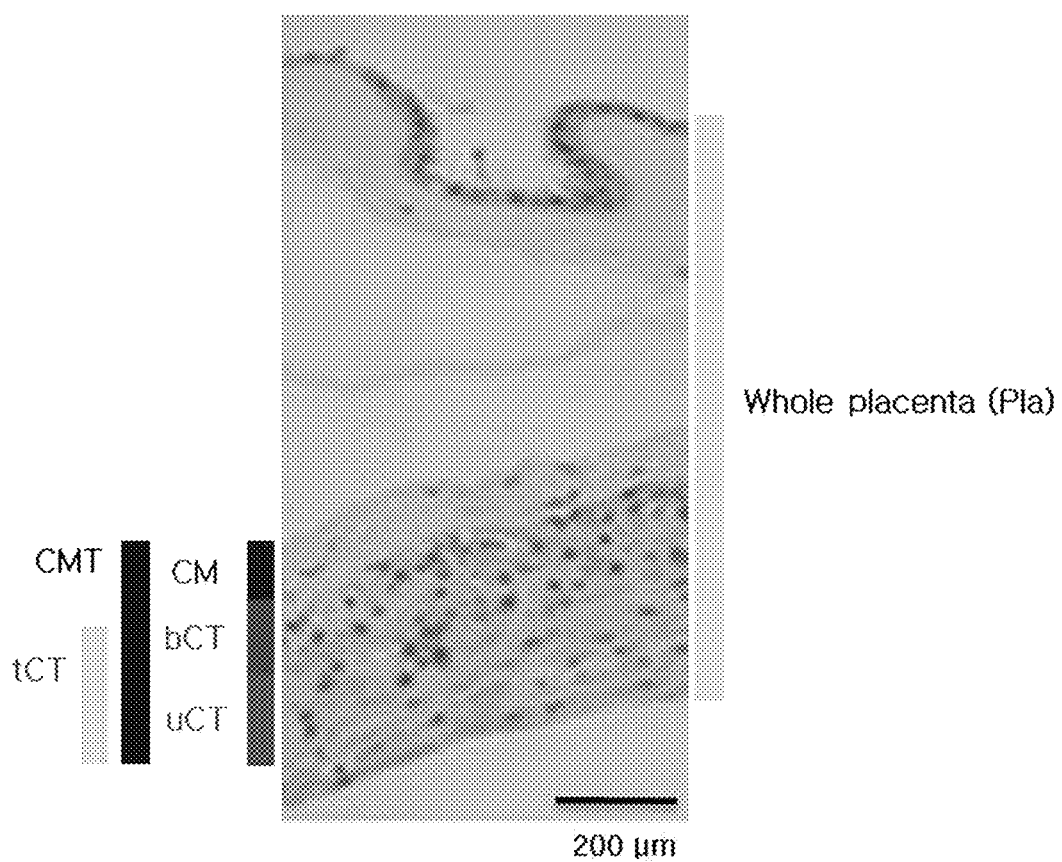
FIG. 1 is a diagram illustrating cross-sectional photographs of a chorionic membrane (CM), a chorionic membrane and chorionic trophoblast layer (CMT), a total chorionic trophoblast layer (tCT), an upper portion of chorionic trophoblast layer (uCT), and a basal portion of chorionic trophoblast layer (bCT) which are parts of the tissues of the placenta (Pla).

In the present invention, the "placenta" refers to a tissue in vivo made for the fetus during pregnancy and has a disk form having a weight of 500 to 600 g, a diameter of 15 to 20 cm, and a thickness of 2 to 3 cm. One side of the placenta is in contact with the mother and the other side thereof is in contact with the fetus, and nutrients and oxygen are transferred between the blood of the mother and the blood vessel of the fetus therebetween. The placenta may be largely divided into three layers of the amnion membrane, the chorionic membrane, and the decidua, and more particularly, into the amniotic epithelium, the amnion membrane, the chorionic membrane, the chorionic trophoblast layer, and the decidua. A cross-sectional view of the placenta is briefly illustrated in FIG. 1.

In the present invention, the "basal portion of chorionic trophoblast layer" refers to a tissue layer corresponding to a thickness of generally about 5 to 6 mm, as a tissue corresponding to a thickness of 20 to 30% of the adjacent (close) portion to a chorionic membrane of the chorionic trophoblast layer positioned between the chorionic membrane and the decidua.

In the present invention, the "chorionic trophoblast layer" refers to a tissue of attaching an egg to the uterine wall and supplying nutrients to the embryo, as an ectoderm layer of the embryo positioned outside the germinal vesicles. The chorionic membrane and the amniotic membrane are derived from the chorionic trophoblast layer and an intracellular layer of the chorionic trophoblast layer covers the villi and is called a cell cytotrophoblast.

In the present invention, the "chorionic membrane" refers to a cellular layer of the outermost layer of an embryo in a human embryology.

In the present invention, the "decidua" refers to the uterine mucosa fallen out after expulsion.

The stem cells derived from the basal portion of chorionic trophoblast layer according to the present invention may be obtained by culturing and then collecting cells obtained by performing enzyme reaction by adding an enzyme solution to the basal portion of chorionic trophoblast layer tissue isolated from the placenta in a medium added with fetal bovine serum and antibiotics without using growth factors. The enzyme includes trypsin, collagenase, dispase, DNase, RNase, protease, lipase, hyaluronidase, elastase, and the like, but is not limited thereto. The collagenase includes collagenase A, I, II, III, or IV.

The stem cells derived from the basal portion of chorionic trophoblast layer according to the present invention exhibit the following features:
  (a) a morphological feature in a fibroblastic cell shape;
  (b) a proliferation capacity for a long period so as to reach the passage number of 25 to 30 or more;
  (c) a differentiation capacity into adipogenic, chondrogenic, or osteogenic;
  (d) a colony formation capacity;
  (e) positive immunological characteristics for CD44, CD73, CD90, and CD105; and
  (f) negative immunological characteristics for CD31, CD34, CD45, and HLA-DR.

The stem cells derived from the basal portion of chorionic trophoblast layer according to the present invention may be differentiated into different kinds of cells, and for example, may be differentiated into various kinds of cells, such as adipogenic, chondrogenic, osteogenic, neuron, ligament, and tenocyte, but the present disclosure is not limited thereto.

In the present invention, the "differentiation" generally refers to a phenomenon in which a relatively simple limit is divided into two or more qualitatively different parts and particularly, means a phenomenon in which different structures or functions are specified while the cells are divided, proliferated, and grown, that is, forms or functions are changed so that cells, tissues, and the like of the organism perform given tasks. On the other hand, the "non-differentiation" means a state in which the aforementioned differentiation does not occur and features as the stem cells are yet included.

A method of differentiating the stem cells may be performed according to an existing known method and is not particularly limited thereto. For example, preferably, the method may be a method of differentiating the stem cells into the adipogenic by culturing the stem cells in a medium including dexamethasone, indomethacin, insulin, and 3-isobutyl-1-methylxanthine (IBMX); a method of differentiating the stem cells into the chondrogenic by culturing the stem cells in a medium including dexamethasone, bone morphogenetic protein 6 (BMP-6), transforming growth factor beta (TGF-β), ascorbic acid, and L-proline; a method of differentiating the stem cells into the osteogenic by culturing the stem cells in a medium including dexamethasone, ascorbic acid, β-glycerophosphate, and ascorbic acid-2-phosphate; and the like.

As a method of measuring the degree of differentiation of the stem cells derived from the basal portion of chorionic trophoblast layer differentiated by the above-described method, a parenchymal cell analysis method, an immunocytochemical method, a method of measuring a cell surface marker or a change in form by using a PCR or a gene-expression profile, a method of examining a morphologic change of the cells by using an optical microscope or a confocal microscope, a method of measuring a change in a gene-expression profile, and the like, which are known in the related art, may be used, but is not limited thereto. Preferably, RT-PCR, an oil-red O staining method, a safranin O staining method, a Type II collagen immunohistochemical staining method, an alkaline phosphate (ALP) staining method, an alizarin red S staining method, or the like may be used.

The stem cells derived from the basal portion of chorionic trophoblast layer (bCT) according to the present invention exhibit uniform growth characteristic, and superb proliferation and differentiation characteristic as compared with the conventional stem cells derived from the whole placenta or other tissues, and exhibit an excellent tissue regeneration effect in a tissue defect animal model.

Accordingly, the present disclosure provides a cellular therapeutic agent including stem cells derived from the basal portion of chorionic trophoblast layer or cells differentiated from the stem cells as an active ingredient.

The differentiated cells are not particularly limited, but include adipogenic, chondrogenic, osteogenic, neuron, ligament, tenocyte, and the like and may be selected according to a therapeutic purpose.

The term "cellular therapeutic agent" in the present invention, as a drug (U.S. FDA regulations) used for treating, diagnosing, and preventing by using cells and tissues prepared through isolation from the human, culture, and a specific manipulation, means a drug used for treating, diagnosing, and preventing of diseases by using the cells through a series of actions such as in vitro proliferating and screening living self, homogeneous, or heterogeneous cells for restoring functions of cells or tissues, changing a biological characteristic of the cells by another method, and the like.

The stem cells derived from the basal portion of chorionic trophoblast layer according to the present invention may be used in various kinds of treatment protocols which are controlled, reinforced, treated, or replaced by engrafting, transplanting, or infusing a cell colony of tissues or organs of the body, for example, a colony of the stem cells or the differentiated cells. The stem cells derived from the basal portion of chorionic trophoblast layer (bCT) of the present disclosure may become a new or changed tissue or be bonded with a biological tissue or structure by replacing or reinforcing an existing tissue.

Preferably, the cellular therapeutic agent of the present disclosure may be used for treating cartilage damage, cartilage defect, bone defect, tendon-ligament defect, or fat tissue defect.

In the present invention, the "cartilage defect" has a meaning including damage, defect, or lack of the cartilage included in the body, and for example, includes cartilage injury, cartilage tear, chondromalacia, cartilage necrosis, osteochondritis, cartilage loss, osteoarthritis, or the like, but the present disclosure is not limited thereto.

Furthermore, the stem cells derived from the basal portion of chorionic trophoblast layer according to the present invention are transplanted into the joint to treat lesions of the articular cartilage or transplanted into a tendon or ligament portion to be used for treatment or prevention. For example, the stem cells derived from the basal portion of chorionic trophoblast layer according to the present invention are transplanted into the joint or the tendon or ligament portion to promote the recovery or the adjustment to the damaged portion of the tissue or may be used for reconfiguring the tissue of the joint (for example, knee joint and the like) by using a material derived from the stem cells such as a cartilage tissue constructs derived from the basal portion of chorionic trophoblast layer according to the present invention or treating the tissue by methods such as regeneration.

A preferable transplantation amount of the cellular therapeutic agent according to the present invention varies according to a state and a weight of the object, the degree of the disease, a drug form, and transplantation route and period, but may be properly selected by those skilled in the art. The transplantation may be performed once or several times a day, and the transplantation amount does not limit the scope of the present disclosure even in any way.

The stem cells derived from the basal portion of chorionic trophoblast layer (bCT) according to the present invention exhibit excellent proliferation and differentiation and an excellent tissue regeneration effect.

Accordingly, the present disclosure provides a composition for regenerating tissues including stem cells derived from the basal portion of chorionic trophoblast layer or cells differentiated from the stem cells as an active ingredient.

The tissues are not particularly limited, but include tissues such as cartilage, fat, bone, nerve, ligament, and tendon.

The cartilage includes hyaline cartilage, fibrocartilage, elastic cartilage, or the like and for example, articular cartilage, ear cartilage, nasal cartilage, elbow cartilage, meniscus, knee cartilage, costal cartilage, ankle cartilage, tracheal cartilage, laryngeal cartilage, or spinal cartilage, but the present disclosure is not limited thereto.

The fat includes all fats regardless of a body position, and for example, includes subcutaneous fat, omentum, mesentery, bone marrow fat, retroperitoneal fat, and the like, but is not limited thereto.

Hereinafter, the present disclosure will be described in more detail with reference to the following Examples. Examples are to describe the present disclosure in detail and the scope of the present disclosure is not limited by Examples.

Example 1: Preparing of Stem Cells Derived from Basal Portion of Chorionic Trophoblast Layer which is a Part of the Tissues of Placenta The placenta was collected from the mother agreeing on donation in a normal cesarean delivery at the Samsung Seoul Hospital according to a guideline for clinical test ethics commission of the Samsung Seoul Hospital. The collected placenta was put in a sterile container and then transferred, an amniotic membrane was removed from the transferred placenta tissue, and then a basal portion of chorionic trophoblast layer tissue which corresponds to a thickness of about 25% of an adjacent (close) portion to the chorionic membrane of the total chorionic trophoblast layer (tCT) positioned between a chorionic membrane (CM) and decidua (DC) was carefully isolated by using sterilized forcep W and knife. The isolated basal portion of chorionic trophoblast layer tissue was transferred on 150 mm dish and washed 8 to 10 times by using PBS to remove blood and blood cells. The washed basal portion of chorionic trophoblast layer tissue was transferred to a 50 ml tube, added with a DMEM medium including 0.2% collagenase, and then reacted for 2 to 3 hours by using an agitator at 37° C. to obtain cells derived from the basal portion of chorionic trophoblast layer. The obtained cells derived from the basal portion of chorionic trophoblast layer were filtered with a mesh of 70 μm to remove a non-decomposed tissue, added with a DMEM medium including fetal bovine serum and antibiotics and then centrifuged for 4 min at 25° C. and 1000 rpm. A supernatant was removed, and then the remaining precipitated cells were added with a DMEM medium including fetal bovine serum and antibiotics without a growth factor and cultured under a condition of 37° C. and 5% $CO_2$. The stem cells derived from the basal portion of chorionic trophoblast layer was obtained by screening the cells attached to the bottom of the culture container from the culture.

Comparative Example 1: Preparing of Stem Cells Derived from Other Tissues 1-1. Preparing of Stem Cells Derived from Whole Placenta The whole placenta tissue was minced and washed with phosphate buffered saline (PBS) to remove blood and blood cells from the placenta tissue. The washed placenta tissue was added with a DMEM medium including 0.2% collagenase and reacted by using an agitator at 37° C. to obtain placenta cells. The obtained placenta cells were filtered with a mesh of 70 μm to remove a non-degraded tissue, added with a DMEM medium including fetal bovine serum and antibiotics, and then centrifuged for 4 min at 25° C. and 1000 rpm. A supernatant was removed, and the remaining precipitated cells were added with a DMEM medium including fetal bovine serum and antibiotics without a growth factor and cultured under a condition of 37° C. and 5% $CO_2$. The stem cells derived from the whole placenta (Pla) were obtained by screening the cells attached to the bottom of the culture container from the culture.

1-2. Preparing of Stem Cells Derived from a Part of Tissues of Placenta

Tissues of a chorionic membrane (CM), a chorionic membrane and chorionic trophoblast layer (CMT), a total chorionic trophoblast layer (tCT), and an upper portion of chorionic trophoblast layer (uCT) which were parts of the tissues of the placenta were isolated, respectively. More particularly, an amniotic membrane was peeled from the whole placenta tissue by using forcep W and a knife and a decidua was carefully removed to isolate the chorionic membrane and chorionic trophoblast layer (CMT), and then a part of the CMT was isolated to the chorionic membrane (CM) and the total chorionic trophoblast layer (tCT). In order to isolate the upper portion of chorionic trophoblast layer (uCT) from the total chorionic trophoblast layer (tCT) tissue, a tissue corresponding to about 75% thickness of an adjacent (close) portion to the decidua in the tCT positioned between the CM and the DC except for the basal portion of chorionic trophoblast layer of Example 1 was carefully isolated by using sterilized forcep W and knife. The partial placenta tissues isolated through the process were transferred to a 150 mm dish and washed 8 to 10 times by using PBS to remove blood and blood cells. The washed partial placenta tissues were transferred to a 50 ml tube, added with a DMEM medium including 0.2% collagenase, and reacted for 2 to 3 hours by using an agitator at 37° C. to obtain cells derived from the CM, the CMT, the tCT, and the uCT, respectively. The obtained cells were filtered with a mesh of 70 μm to remove a non-decomposed tissue, added with a DMEM medium including fetal bovine serum and antibiotics, and then centrifuged for 4 min at 25° C. and 1000 rpm. A supernatant was removed, a DMEM medium including fetal bovine serum and antibiotics without a growth factor was added in the remaining precipitated cells, and the cells were cultured under a condition of 37° C. and 5% $CO_2$. The stem cells derived from the cells derived from the CM, the CMT, the tCT, and the uCT were obtained by screening the cells attached to the bottom of the culture container from the culture, respectively.

1-3. Isolation of Stem Cells Derived from Bone Marrow

Bone marrow was transferred to a 50 ml tube, washed with the same amount of PBS, and centrifuged for 10 min at 25° C. and 2580 rpm. After the washing process was repeated twice, a supernatant was removed, and then the remaining precipitated bone marrow was suspended with the same amount of PBS (total 5 ml), and then the solution was slowly transferred onto a prepared Ficoll solution of 25 ml and centrifuged for 30 min at 25° C. and 2580 rpm. Only an intermediate cell layer of three layers isolated by the density difference was isolated and washed, and then centrifuged for 5 min at 25° C. and 2580 rpm. The cells obtained through the process were added with a DMEM medium including fetal bovine serum and antibiotics without a growth factor and cultured under a condition of 37° C. and 5% $CO_2$ to obtain stem cells derived from the bone marrow.

1-4. Isolation of Stem Cells Derived from Umbilical Cord Blood

Umbilical cord blood was transferred to a 50 ml tube, washed with the same amount of PBS, and centrifuged for 10 min at 25° C. and 2580 rpm. After the washing process was repeated twice, a supernatant was removed, and then the remaining precipitated umbilical cord blood was suspended with the same amount of PBS (total 5 ml), and then the solution was slowly transferred onto a prepared Ficoll solution of 25 ml and centrifuged for 30 min at 25° C. and 2580 rpm. Only an intermediate cell layer of three layers isolated by the density difference was isolated and washed, and then centrifuged for 5 min at 25° C. and 2580 rpm. The cells obtained through the process were added with a DMEM medium including fetal bovine serum and antibiotics without a growth factor and cultured under a condition of 37° C. and 5% $CO_2$ to obtain stem cells derived from the umbilical cord blood.

1-5. Isolation of Stem Cells Derived from Adipose or Synovium

An adipose or synovium tissue was transferred to a 150 mm dish and washed 2 to 3 times by using PBS to remove blood and blood cells. After the adipose or synovium tissue was finely cut, each tissue was transferred to a 50 ml tube, added with a DMEM medium including 0.2% collagenase, and then reacted by using an agitator at 37° C. to obtain adipose or synovium cells. The obtained adipose or synovium cells were filtered with a mesh of 70 μm to remove a non-decomposed tissue, added with a DMEM medium including fetal bovine serum and antibiotics, and centrifuged for 4 min at 25° C. and 1000 rpm. A supernatant was removed, and then the remaining precipitated cells were added with a DMEM medium including fetal bovine serum and antibiotics without a growth factor and cultured under a condition of 37 C and 5% $CO_2$ to obtain stem cells derived from adipose or synovium.

Example 2: Subculture of Stem Cells Derived from Basal Portion of Chorionic Trophoblast Layer which is a Part of the Tissues of Placenta The stem cells derived from the basal portion of chorionic trophoblast layer which was a part of the tissues of the placenta obtained in Example 1 were washed with PBS and cultured by replacing a DMEM medium including fetal bovine serum and antibiotics without a growth factor every 2 to 3 days. When the stem cells were grown 80% or more, the stem cells was treated with TryPLE to be isolated from the culture container, and the isolated stem cells were diluted in a ratio of 1/4 and then cultured in another culture container to perform a subculture. While repetitively performing the subculture, the passage number which was not sub-cultured at all was measured, and cell forms before the subculture (P0) and after long-term subculture were observed with a microscope. Further, using the stem cells derived from the whole placenta (Pla) obtained in Comparative Example 1, the subculture was performed by the same method and then cell forms before the subculture (P0) and after long-term subculture were observed with a microscope. The results are illustrated in FIGS. 2 to 3.

Figure 2:
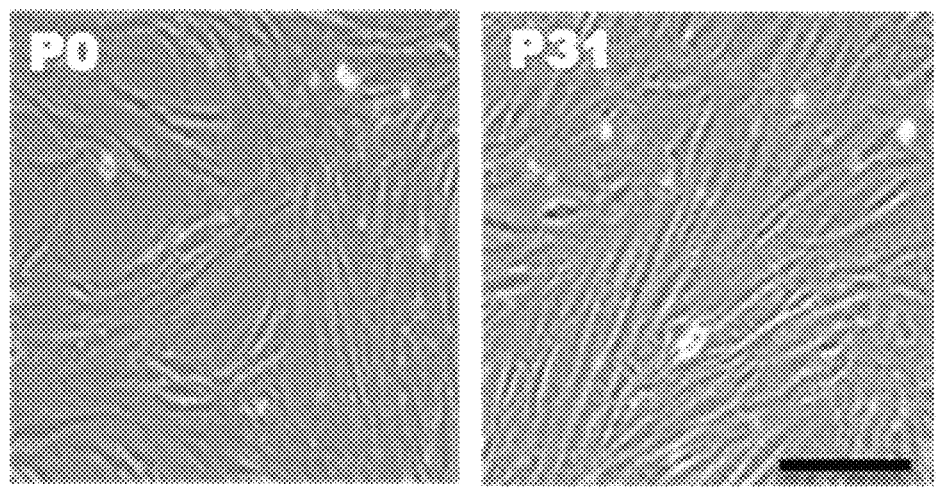
FIG. 2 is a diagram illustrating photographs (×100) which are obtained by observing, by a microscope, cell forms before subculture (P0) and after long-term subculture (P31) of stem cells derived from the basal portion of chorionic trophoblast layer (bCT) according to an exemplary embodiment of the present invention.

As illustrated in FIG. 2, it was verified that the stem cells derived from the basal portion of chorionic trophoblast layer (bCT) according to the present invention exhibited excellent proliferation until the passage number reached 31, and long-term culture was possible.

Figure 3:
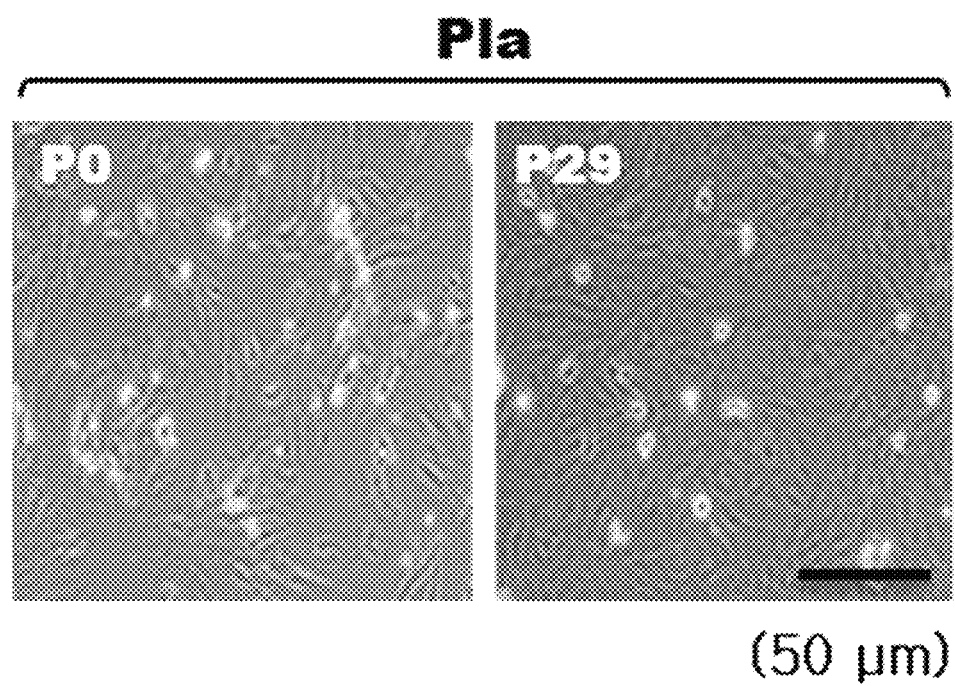
FIG. 3 is a diagram illustrating photographs (×100) which are obtained by observing, by a microscope, cell forms before subculture (P0) and after long-term subculture (P29) of stem cells derived from the whole placenta.

Further, as illustrated in FIG. 3, it was verified that the stem cells derived from the whole placenta (Pla) exhibited a fibroblast-shaped morphological characteristic from an early stage of the subculture and a plurality of cells having different shapes other than one shape were mixed. That is, as compared with FIG. 2, in the stem cells derived from the basal portion of chorionic trophoblast layer before and after the subculture, only single cells were specifically maintained, but in the stem cells derived from the whole placenta, the cells having different shapes were mixed.

Example 3: Analysis of Colony Formation Capacity of Stem Cells Derived from Basal Portion of Chorionic Trophoblast Layer which is a Part of the Tissues of Placenta A population doubling time and a colony formation capacity of the stem cells derived from the basal portion of chorionic trophoblast layer as a part of the tissues of the placenta obtained in Example 1 were verified. More particularly, in the stem cells derived from the basal portion of chorionic trophoblast layer obtained in Example 1, the first subculture was performed by the method of Example 2, and the stem cells were seeded by $5 \times 10^3$ in a dish of 100 mm at the time when the subculture was completed and then cultured in a DMEM medium including fetal bovine serum and antibiotics without a growth factor for 10 days. A time (population doubling time) taken to double the number of stem cells from P2 to P6 was measured and the number of colonies formed in the stem cells was counted by performing a Giemsa stain method in the cultured stem cells. Further, by using the stem cells derived from the whole placenta, other partial placenta tissues, and other tissues obtained in Comparative Example 1, the population doubling time and the colony formation capacity were measured by the same method. In the case of the colony formation capacity, the result value of the stem cells derived from the whole placenta was converted to 100%. The results are illustrated in FIGS. 4 to 5.

Figure 4:
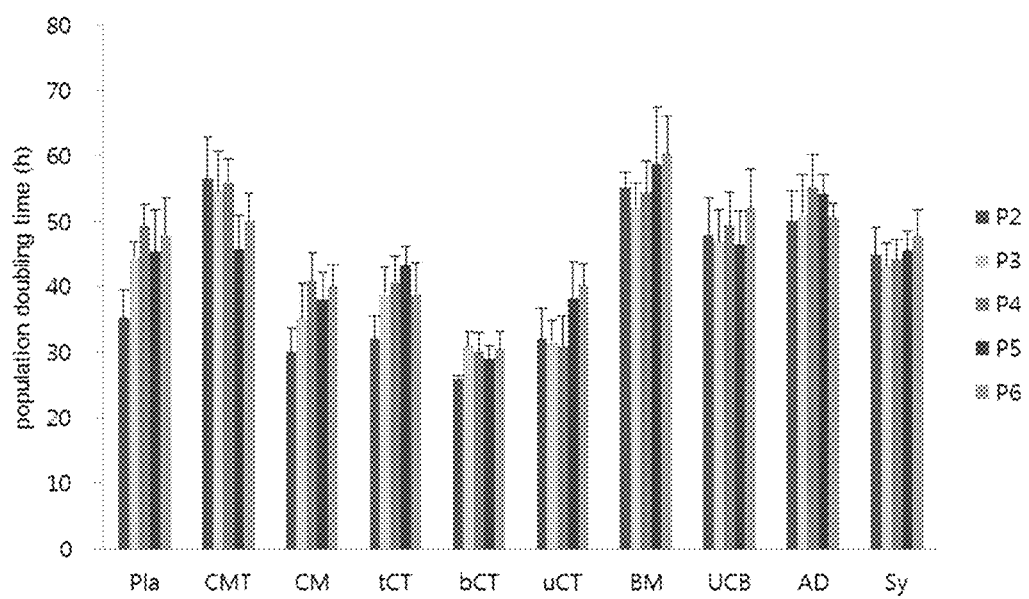
FIG. 4 is a diagram illustrating population doubling times of stem cells derived from the whole placenta, each fine tissue of the placenta, and other tissues.

As illustrated in FIG. 4, it was verified that the stem cells derived from the basal portion of chorionic trophoblast layer (bCT) according to the present invention had a much short population doubling time as compared with the stem cells derived from the whole placenta, other partial placenta tissues, and other tissues and the cell proliferation was rapid.

Figure 5:
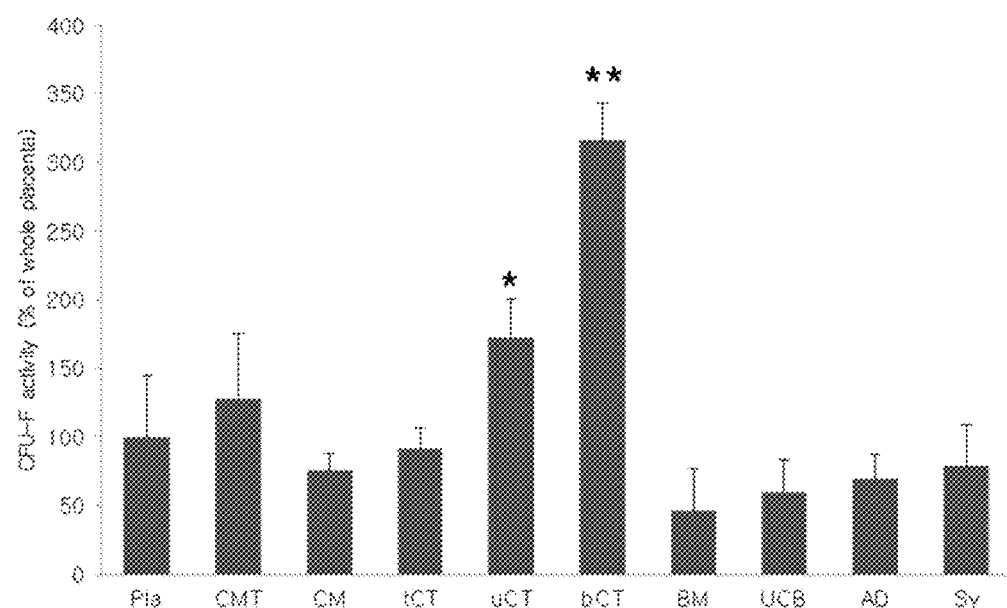
FIG. 5 is a diagram illustrating colony formation units of stem cells derived from the whole placenta, each fine tissue of the placenta, and other tissues.

As illustrated in FIG. 5, it was verified that the stem cells derived from the basal portion of chorionic trophoblast layer (bCT) according to the present invention exhibited a significantly excellent colony formation capacity as compared with the stem cells derived from the whole placenta, other partial placenta tissues, and other tissues.

Example 4: Analysis of Surface Marker of Stem Cells Derived from Basal Portion of Chorionic Trophoblast Layer which is a Part of the Tissues of Placenta In order to verify immunological properties of the stem cells derived from the basal portion of chorionic trophoblast layer as a part of the tissues of the placenta obtained in Example 1, the following test was performed. First, the stem cells derived from the basal portion of chorionic trophoblast layer were washed with PBS and treated with TryPLE to collect the stem cells and centrifuged for 4 min at 1000 rpm. After the supernatant was removed, in order to suppress non-specific binding, the stem cells were washed by adding a mixed solution of 2% FBS and PBS was added and then centrifuged for 5 min at 1000 rpm. After the supernatant was removed, the stem cells were suspended in the PBS and divided in a flowcytometer-dedicated round flask by $1 \times 10^5$ cells. A PE-conjugated mouse anti-human monoclonal antibody was added herein, respectively, and the stem cells were incubated for 30 min in ice and then centrifuged for 5 min at 1000 rpm. After the supernatant was removed again, the stem cells were washed with the PBS and centrifuged for 5 min at 1000 rpm. The process was repeated two times. Finally, after the supernatant was removed, the stem cells were singled and the immunological properties were analyzed by using a flowcytometer (FACS). Further, immunological properties of the stem cells derived from the whole placenta, other partial placenta tissues, and other tissues obtained in Comparative Example 1 were analyzed by the same method. The results are illustrated in Table 1 and FIG. 6.

TABLE 1

|  | CD31 | CD34 | CD45 | CD73 | CD90 | CD105 | HLA-DR | CD-44 |
| --- | --- | --- | --- | --- | --- | --- | --- | --- |
| Pla | 0.0% | 0.0% | 0.0% | 98.4% | 92.4% | 92.4% | 0.0% | 92.9% |
| CMT | 0.0% | 0.0% | 0.0% | 98.0% | 91.7% | 96.9% | 0.0% | 98.6% |
| CM | 0.0% | 0.0% | 0.0% | 99.8% | 100.0% | 98.1% | 0.0% | 96.6% |
| tCT | 0.0% | 0.0% | 0.0% | 97.6% | 96.6% | 98.1% | 0.0% | 92.7% |
| bCT | 0.0% | 0.0% | 0.0% | 97.9% | 100.0% | 100.0% | 0.0% | 95.6% |
| uCT | 0.0% | 0.0% | 0.0% | 99.1% | 96.0% | 98.0% | 0.0% | 93.2% |
| BM | 0.0% | 0.0% | 0.0% | 98.7% | 100.0% | 98.2% | 0.0% | 94.2% |
| UCB | 0.0% | 0.0% | 0.0% | 93.8% | 92.4% | 99.9% | 0.0% | 93.9% |
| AD | 0.0% | 0.0% | 0.0% | 98.1% | 99.5% | 99.3% | 0.0% | 92.0% |
| Sy | 0.0% | 0.0% | 0.0% | 99.9% | 98.2% | 99.6% | 0.0% | 80.4% |

Figure 6:
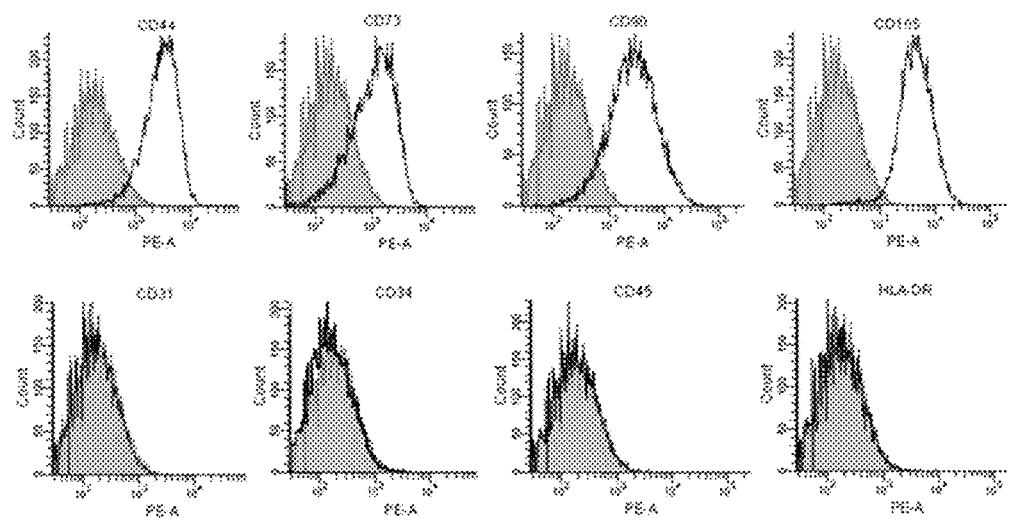
FIG. 6 is a diagram illustrating a parenchymal cell analysis result for verifying a surface factor expression characteristic of the stem cells derived from the basal portion of chorionic trophoblast layer (bCT) according to the present invention.

As shown in Table 1 and FIG. 6, it was verified that the stem cells derived from the basal portion of chorionic trophoblast layer (bCT) according to the present invention exhibited positive marker expression characteristics for CD44, CD73, CD90, and CD105 and negative marker expression characteristics for CD31, CD34, CD45, and HLA-DR.

Example 5: Verification of Ability to Differentiate into Chondrocyte of Stem Cells Derived from Basal Portion of Chorionic Trophoblast Layer which is a Part of the Tissues of the Placenta In order to verify differentiation into chondrocyte of the stem cells derived from the basal portion of chorionic trophoblast layer which was a part of the tissues of the placenta obtained in Example 1, the stem cells were cultured for 3 weeks in a known chondrogenic differentiation induced medium (a DMEM medium including 0.1 μM dexamethasone, 50 μg/ml ascorbic acid, 40 μg/ml L-proline, 10 ng/ml TGF-β3, 500 ng/ml BMP-6, and 50 mg/ml ITS premix) to induce the differentiation into the chondrogenic. In order to measure the degree of the differentiation of the stem cells into the chondrogenic, a safranin-O staining method and an immunohistochemical staining method using Type II collagen were performed according to the existing known method. Further, the degree of differentiation of the stem cells derived from the whole placenta, other partial placenta tissues, and other tissues obtained in Comparative Example 1 into chondrogenic was measured by the same method. The results are illustrated in FIGS. 7 to 9.

Figure 7:
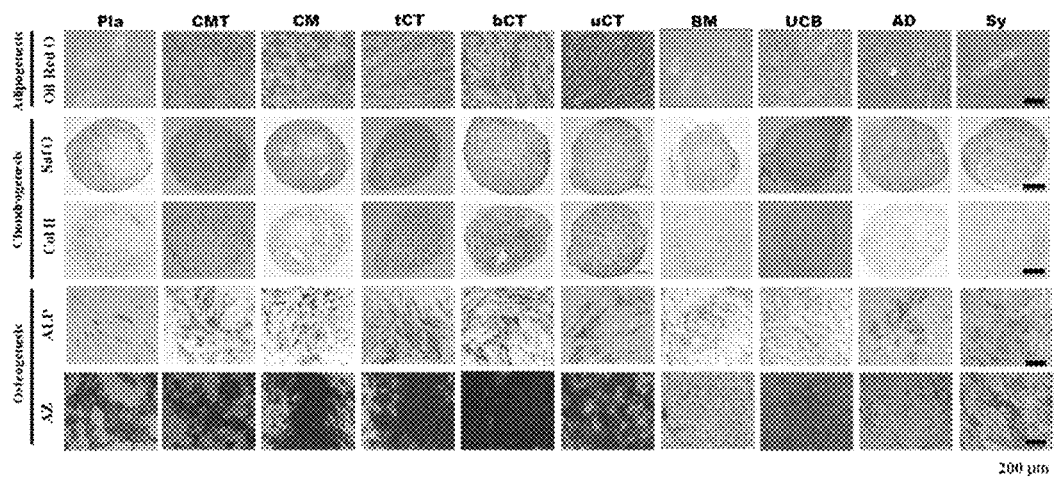
FIG. 7 is a diagram illustrating staining results for observing the degrees of differentiations of the stem cells derived from the whole placenta, each fine tissue of the placenta, and other tissues into adipogenic(adipogenesis), chondrogenic (chondrogenesis), or osteogenic(osteogenesis), respectively.
Figure 8:
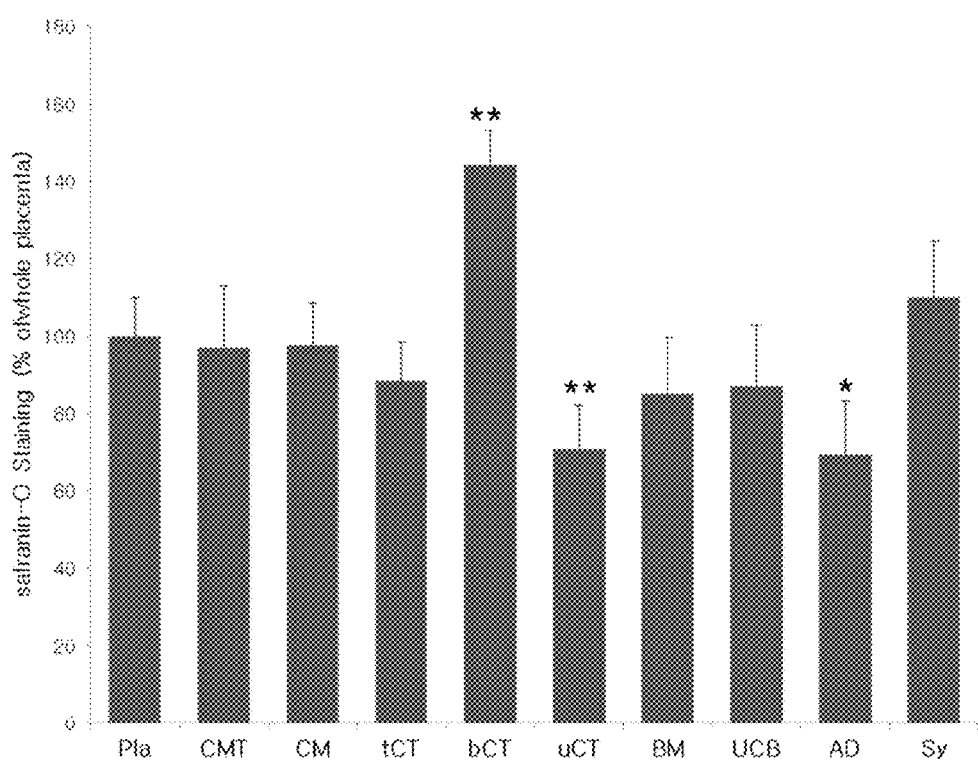
FIG. 8 is a diagram illustrating quantified results obtained after Safranin-O staining for observing the degree of differentiation of the stem cells derived from the whole placenta, each fine tissue of the placenta, and other tissues into chondrogenic.
Figure 9:
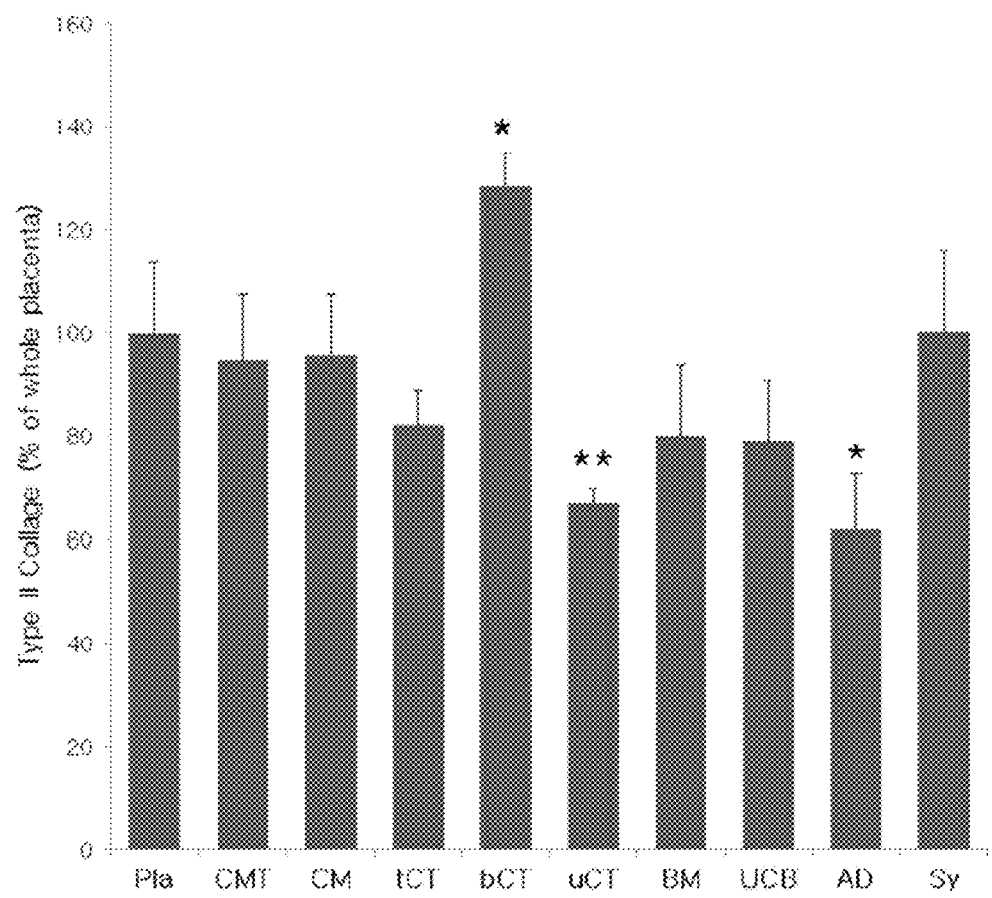
FIG. 9 is a diagram illustrating quantified results obtained after performing immunohistochemical staining by using Type II collagen for observing the degree of the differentiation of the stem cells derived from the whole placenta, each fine tissue of the placenta, and other tissues into chondrogenic.

As illustrated in FIGS. 7 to 9, it was verified that the stem cells derived from the basal portion of chorionic trophoblast layer (bCT) according to the present invention had the excellent ability of differentiation to the chondrogenic which may be uniformly differentiated into the chondrocyte as compared with the stem cells derived from the whole placenta, other partial placenta tissues, and other tissues.

Example 6: Verification of Ability to Differentiate into Osteoblast of Stem Cells Derived from Basal Portion of Chorionic Trophoblast Layer which is a Part of the Tissues of Placenta In order to verify differentiation into osteoblast of the stem cells derived from the basal portion of chorionic trophoblast layer which was a part of the tissues of the placenta obtained in Example 1, the stem cells were cultured for 4 weeks in a known osteogenic differentiation induced medium (a DMEM medium including 10% FBS, 1% antibiotics, 100 μM dexamethasone, 50 mM of ascorbic acid-2-phosphate, 10 μM β-glycerophosphate, and 250 μM ascorbic acid) to induce the differentiation into the osteogenic. In this case, at the time when two weeks elapsed after the differentiation induction started, an alkaline phosphate (ALP) staining method was performed according to the existing known method, and at the time when four weeks elapsed, an alizarin red S staining method was performed according to the existing known method to analyze the differentiation into osteogenic. Further, the degree of differentiation of the stem cells derived from the whole placenta, other partial placenta tissues, and other tissues obtained in Comparative Example 1 into osteogenic was measured by the same method. The results are illustrated in FIGS. 7, 10, and 11.

Figure 10:
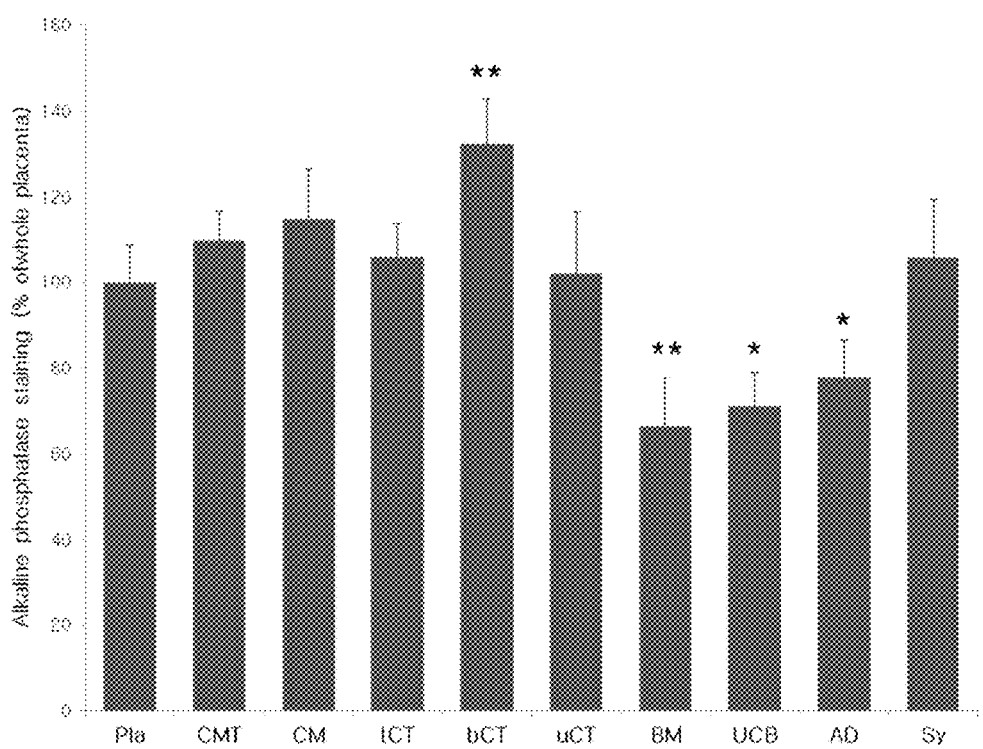
FIG. 10 is a diagram illustrating quantified results obtained after staining with alkaline phosphate for observing the degree of differentiation of the stem cells derived from the whole placenta, each fine tissue of the placenta, and other tissues into osteogenic.
Figure 11:
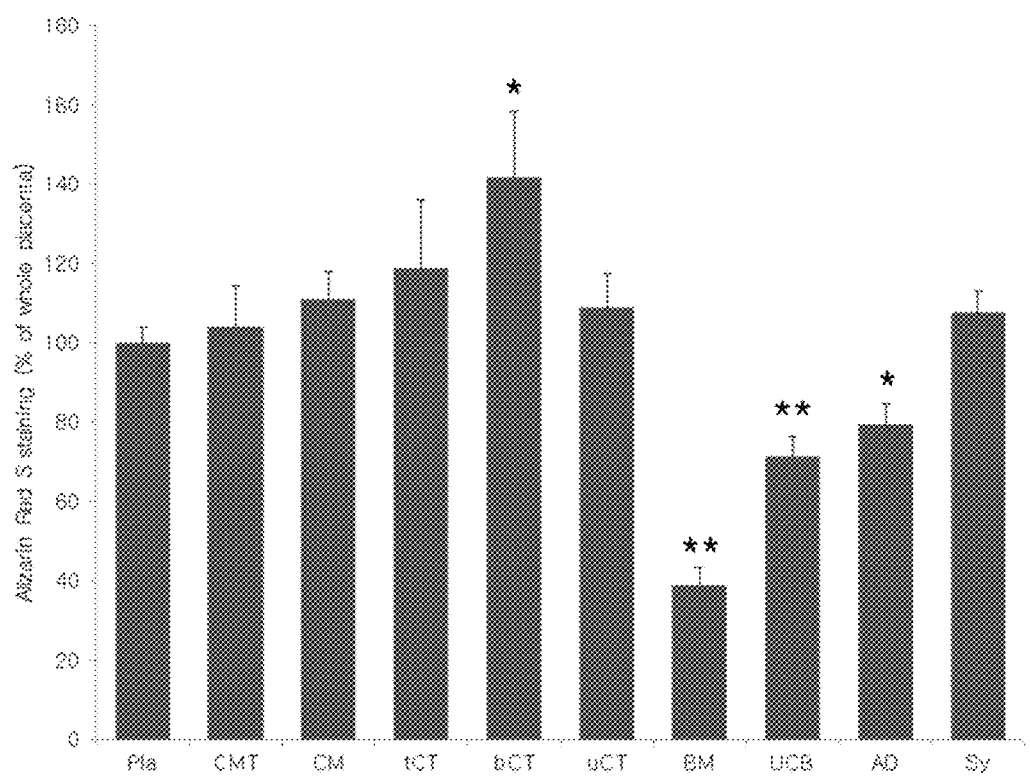
FIG. 11 is a diagram illustrating quantified results obtained after staining with Alizarin red S for observing the degree of differentiation of the stem cells derived from the whole placenta, each fine tissue of the placenta, and other tissues into osteogenic.

As illustrated in FIGS. 7, 10, and 11, it was verified that the stem cells derived from the basal portion of chorionic trophoblast layer (bCT) according to the present invention had the excellent ability of differentiation to the osteogenic which may be uniformly differentiated into the osteoblast as compared with the stem cells derived from the whole placenta, other partial placenta tissues, and other tissues.

Example 7: Verification of Ability to Differentiate into Adipocyte of Stem Cells Derived from Basal Portion of Chorionic Trophoblast Layer which is a Part of the Tissues of the Placenta In order to verify differentiation into adipocyte of the stem cells derived from the basal portion of chorionic trophoblast layer as the part of the tissues of the placenta obtained in Example 1, the stem cells were alternately added with an adipogenic differentiation induced medium (a DMEM medium including 10% FBS, 1% Antibiotics, 1 pM dexamethasone, 20 µM indomethacin, 10 µM insulin, and 50 µM 3-isobutyl-1-methylxanthine (IBMX)) and an adipogenic differentiation induced medium (a DMEM medium including 10% FBS, 1% Anti-biotics, and 10 µM insulin) to induce differentiation into the adipogenic. In order to measure the differentiation of the stem cells into the adipogenic, oil red O staining was performed according to the existing known method. Further, the differentiation of the stem cells derived from the whole placenta, other partial placenta tissues, and other tissues obtained in Comparative Example 1 into adipogenic was measured by the same method. The results are illustrated in FIGS. 7 and 12.

Figure 12:
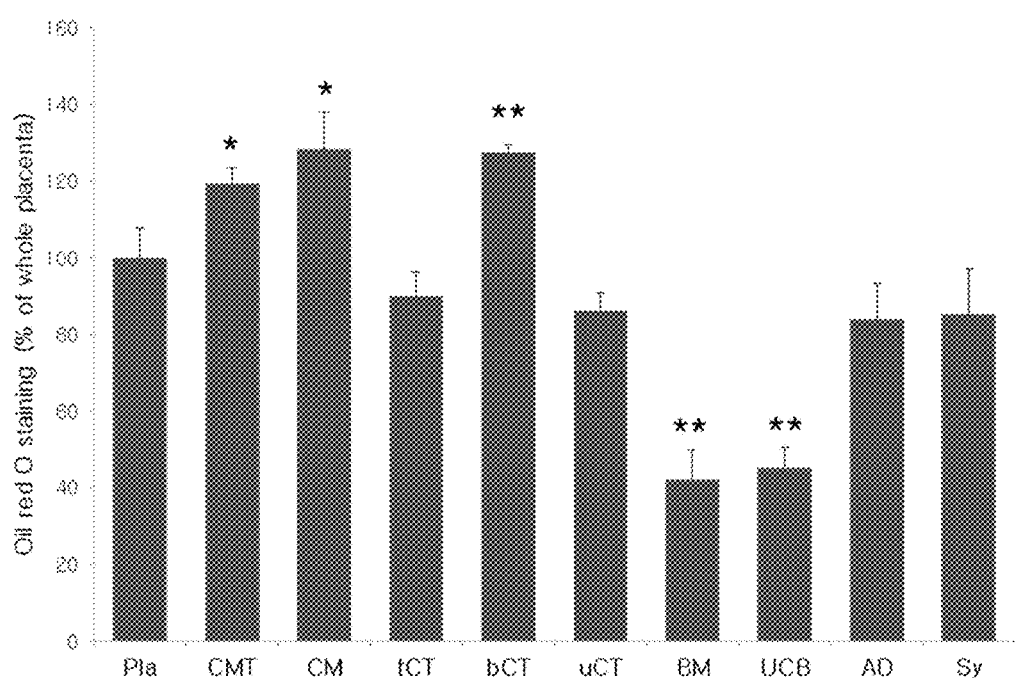
FIG. 12 is a diagram illustrating quantified results obtained after staining with Oil red O for observing the degree of differentiation of the stem cells derived from the whole placenta, each fine tissue of the placenta, and other tissues into adipogenic.

As illustrated in FIGS. 7 and 12, it was verified that the stem cells derived from the basal portion of chorionic trophoblast layer (bCT) according to the present invention had excellent ability of differentiation to the adipogenic which may be uniformly differentiated into the adipocyte as compared with the stem cells derived from the whole placenta, other partial placenta tissues, and other tissues.

Example 8: Verification of Effects as Cellular Therapeutic Agent in Cartilage Damage Animal Model of Stem Cells Derived from Basal Portion of Chorionic Trophoblast Layer which is a Part of the Tissues of the Placenta In order to verify effects of the stem cells derived from the basal portion of chorionic trophoblast layer as a part of the tissues of the placenta obtained in Example 1 as a cellular therapeutic agent in a tissue defect animal model, the following test was performed. More particularly, in order to prepare a rabbit articular cartilage damage animal model, after a health rabbit was selected and anesthetized with a proper amount of Ketamine and Rompun according to a weight, it was verified that the rabbit was sufficiently general-anesthetized, and after the knee joints of both pelvic limbs were shaved and fixed with a plaster while the posture was maintained. The both knee joints were disinfected with povidone, the kneecap was detected and the location was verified, the inside of the knee joints was reached by a paramedian approach along a cut line through the top and the bottom of the knee joint and the inside of the kneecap, the knee joint was bent while the kneecap was bent back outside, and then the inside of the joint was observed. After it was verified that there was no specific pathological finding, a scratch was made with a pointed awl at the top of 1 mm from a front end of intercondylar notch of the kneecap, a hole having a diameter of 3 mm and a depth of 5 mm was made with a drill based on the scratch to damage the cartilage full thickness. As such, it was verified that after 8 weeks and 16 weeks after inducing the cartilage damage, the damage portion was observed and the cartilage damage portion was not naturally healed. After the stem cells derived from the basal portion of chorionic trophoblast layer according to the present invention was mixed with hyaluronic acid by using a syringe, 500 µl was transplanted to the cartilage damage portion made at the right of the animal model (500 µL was sufficiently prepared for convenience of operation by considering a case when the amount of the composition was insufficient or a mistake during operation was made). Thereafter, after the kneecap returned to an original location, a soft tissue around the kneecap was sutured with an absorbent thread and the skin was sutured with a non-absorbent thread. As a positive control group, an equal volume of the mixture of hyaluronic acid and stem cells derived from umbilical cord blood was transplanted into the opposite leg. After it was verified that the rabbit waked up from the anesthesia, the rabbit was allowed to move freely, and painkillers and antibiotics were administrated in order to prevent infection for 5 days after operation. After 8 weeks and 16 weeks elapsed, H&E and Safranin O staining were performed by obtaining pieces of the articular cartilage portion which had performed the damage and the treatment from the rabbit, and a new cartilage was analyzed through quantification using international cartilage repair society (ICRS) macroscopic score. The results are illustrated in FIGS. 13 and 14.

Figure 13:
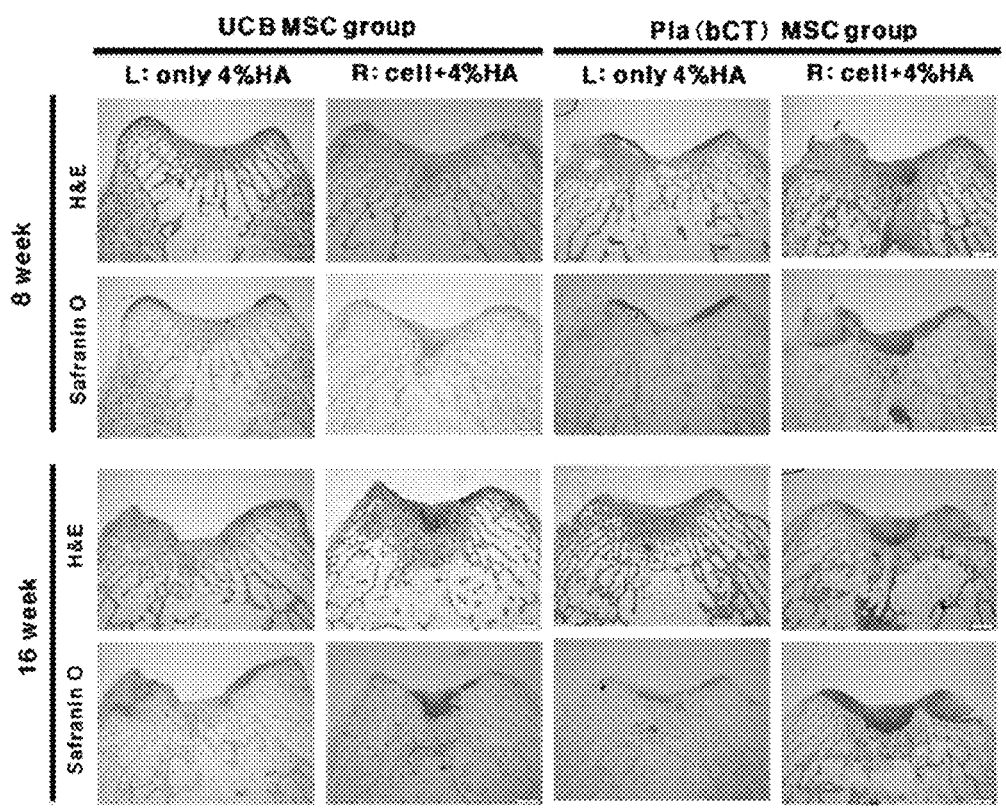
FIG. 13 is a diagram illustrating results of verifying a cartilage regeneration effect through H&E and Safranin-O staining after transplanting the stem cells derived from umbilical cord blood (UCB) or the stem cells derived from a basal portion of chorionic trophoblast layer (bCT) to a cartilage damage animal model.
Figure 14:
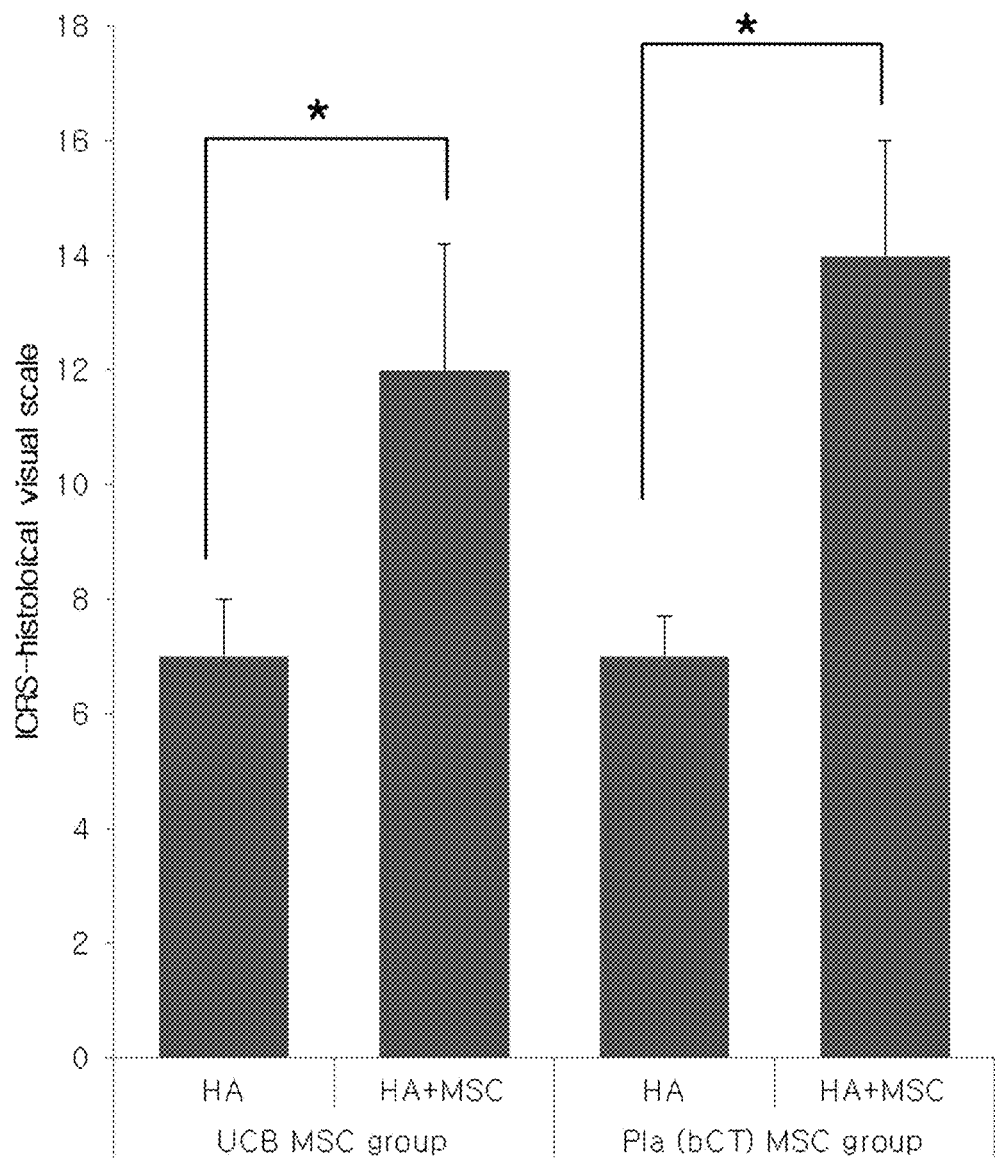
FIG. 14 is a diagram illustrating results of verifying a cartilage regeneration effect through the quantification using international cartilage repair society (ICRS) macroscopic score after transplanting the stem cells derived from umbilical cord blood (UCB) or the stem cells derived from a basal portion of chorionic trophoblast layer (bCT) to a cartilage damage animal model.

As illustrated in FIGS. 13 and 14, a group transplanted with the stem cells derived from the basal portion of chorionic trophoblast layer (bCT) according to the present invention was two times or more larger than the entire thickness of the newly generated cartilage cell layer than a group transplanted with the stem cells derived from the umbilical cord blood. Accordingly, it was verified that the stem cells derived from the basal portion of chorionic trophoblast layer (bCT) can generate the chondrogenic at the damaged articular cartilage portion with excellent efficiency to efficiently treat the articular cartilage damage.

Through the test result, it was verified that the stem cells derived from the existing whole placenta were mixed with the stem cells derived from the partial tissues having various characteristics and thus differentiation into different cells was not uniformly exhibited. However, it was verified that the stem cells derived from the basal portion of chorionic trophoblast layer which was a part of the tissues of the placenta according to the present invention exhibited excellent characteristics as compared with the stem cells derived from the existing whole placenta in terms of excellent differentiation and uniformity for various features of other stem cells. Particularly, the stem cells derived from the basal portion of chorionic trophoblast layer according to the present invention exhibited a consistent pattern in characteristics of growth, proliferation, morphology, and differentiation as compared with the stem cells derived from the chorionic membrane (CM), the chorionic membrane and chorionic trophoblast layer (CMT), the total chorionic trophoblast layer (tCT), and the upper portion of chorionic trophoblast layer (uCT) which are other parts of the tissues of the placenta and exhibited the most excellent characteristic of the stem cells. Therefore, it can be seen that the stem cells derived from the basal portion of chorionic trophoblast layer can improve efficiency of differentiation into a desired cell and be used as a cellular therapeutic agent in various diseases.

We claim:

1. A method for regenerating tissues of a subject in need thereof, comprising transplanting a composition to the subject, wherein the composition comprises stem cells derived from a basal portion of a chorionic trophoblast layer (bCT) which is a part of the tissues of the placenta or cells differentiated from the stem cells as an active ingredient;

wherein the stem cells derived from the bCT are prepared by the following steps:
(a) isolating a chorionic trophoblast layer which is a part of the tissues of the placenta, from placenta;
(b) preparing the bCT which is derived from a tissue corresponding to a thickness of 20 to 30% as a portion adjacent to a chorionic membrane of a total chorionic trophoblast layer positioned between the chorionic membrane and a decidua;
(c) obtaining cells derived from the bCT by treating the bCT with one or more kinds of enzymes selected from the group consisting of trypsin, collagenase, dispase, DNase, RNase, protease, lipase, hyaluronidase, and elastase; and
(d) screening the stem cells from the obtained cells derived from the bCT.

2. The method of claim 1, wherein the tissue is one or more kinds selected from the group consisting of cartilage, fat, bone, nerve, ligament, and tendon.

3. The method of claim 2, wherein the cartilage is hyaline cartilage, fibrocartilage, or elastic cartilage.

4. The method of claim 2, wherein the cartilage is selected from the group consisting of articular cartilage, ear cartilage, nasal cartilage, elbow cartilage, meniscus, knee cartilage, costal cartilage, ankle cartilage, tracheal cartilage, laryngeal cartilage, and spinal cartilage.

5. A method of isolating stem cells from basal portion of a chorionic trophoblast layer (bCT) comprising the following steps:
(a) isolating a chorionic trophoblast layer which is a part of the tissues of the placenta, from placenta;
(b) preparing the bCT which is derived from a tissue corresponding to a thickness of 20 to 30% as a portion adjacent to a chorionic membrane of a total chorionic trophoblast layer positioned between the chorionic membrane and a decidua;
(c) obtaining cells derived from the bCT by treating the bCT with one or more kinds of enzymes selected from the group consisting of trypsin, collagenase, dispase, DNase, RNase, protease, lipase, hyaluronidase, and elastase; and
(d) screening the stem cells from the obtained cells derived from the bCT.

6. The method of claim 5, wherein preparing the bCT in step (b) is performed by a using sterilized forceps and a knife.

7. The method of claim 5, wherein screening the stem cells in step (d) is performed by a method comprising the following steps:
(i) culturing the obtained cells derived from the bCT from step (c) in a culture container; and
(ii) screening the attached cultured cells wherein the attached cultured cells are attached to the bottom of the culture container.

8. The method of claim 5, further comprising the step of transplanting the stem cells from basal portion of chorionic trophoblast layer (bCT) in a patient in need of a cellular therapeutic agent.

9. The method of claim 8, wherein the cellular therapeutic agent is used to treat a patient having cartilage damage, cartilage defect, bone defect, tendon-ligament defect, or fat tissue defect.

10. The method of claim 9, wherein the cartilage defect is selected from the group consisting of cartilage injury, cartilage tear, chondromalacia, cartilage necrosis, osteochondritis, cartilage loss, and osteoarthritis.

* * * * *